(12) United States Patent
Trock

(10) Patent No.: US 10,146,911 B2
(45) Date of Patent: Dec. 4, 2018

(54) MEDICAL DEVICES AND RELATED METHODS AND SYSTEMS FOR DATA TRANSFER

(71) Applicant: MEDTRONIC MINIMED, INC., Northridge, CA (US)

(72) Inventor: Adam S. Trock, Burbank, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 503 days.

(21) Appl. No.: 14/922,026

(22) Filed: Oct. 23, 2015

(65) Prior Publication Data

US 2017/0113001 A1 Apr. 27, 2017

(51) Int. Cl.
*A61M 31/00* (2006.01)
*G06F 19/00* (2018.01)

(52) U.S. Cl.
CPC ........ *G06F 19/324* (2013.01); *G06F 19/3418* (2013.01)

(58) Field of Classification Search
CPC .............. G06F 19/324; G06F 19/3418; A61M 2205/3317; A61M 2205/3569; A61M 2205/3584; A61M 2205/52; A61M 5/14212; A61M 5/1723
USPC ......................................................... 604/65
See application file for complete search history.

(56) References Cited

U.S. PATENT DOCUMENTS

| | | | |
|---|---|---|---|
| 3,631,847 A | 1/1972 | Hobbs, II | |
| 4,212,738 A | 7/1980 | Henne | |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | Decant, Jr. et al. | |
| 4,494,950 A | 1/1985 | Fischell | |
| 4,542,532 A | 9/1985 | McQuilkin | |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Jason Flick
(74) *Attorney, Agent, or Firm* — Lorenz & Kopf, LLP

(57) ABSTRACT

Medical devices and related systems and operating methods for communicating data therewith are provided. An exemplary method involves the medical device detecting an interfacing device coupled to the medical device via a physical communications medium, initializing a wireless communications session with the interfacing device in response to detecting the interfacing device, modulating an electrical signal between the interfacing device and the medical device to transmit data from the medical device to the interfacing device via the physical communications medium, and receiving communications, such as acknowledgments of the transmitted data, from the interfacing device via the wireless communications session.

10 Claims, 8 Drawing Sheets

(56) References Cited

U.S. PATENT DOCUMENTS

| | | |
|---|---|---|
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,771,399 A | 9/1988 | Snowden et al. |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,012,411 A * | 4/1991 | Policastro .......... A61B 5/04325 600/485 |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,568,351 B1 | 5/2003 | Barclay et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |

(56) References Cited

U.S. PATENT DOCUMENTS

| | | |
|---|---|---|
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,082,877 B2 | 8/2006 | Jennings, III |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,621,893 B2 | 11/2009 | Moberg et al. |
| 7,627,044 B2 | 12/2009 | Kim et al. |
| 8,474,332 B2 | 7/2013 | Bente, IV |
| 8,674,288 B2 | 3/2014 | Hanson et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(Intensive Diabetes Management, 1995). Insulin Infusion Pump Therapy. pp. 66-78.

(MiniMed, 1996). The MiniMed 506. 7 pages. Retrieved on Sep. 16, 2003 from the World Wide Web: http://web.archive.org/web/19961111054527/www.minimed.com/files/506_pic.htm.

(56) References Cited

OTHER PUBLICATIONS (MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

(56) References Cited

OTHER PUBLICATIONS

Shichiri, Motoaki, et al., "Closed-Loop Glycemic Control with a Wearable Artificial Endocrine Pancreas Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Urban, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

US 10,146,911 B2

MEDICAL DEVICES AND RELATED METHODS AND SYSTEMS FOR DATA TRANSFER

TECHNICAL FIELD

Embodiments of the subject matter described herein relate generally to medical devices, and more particularly, embodiments of the subject matter relate to communicating data with a fluid infusion device.

BACKGROUND

Infusion pump devices and systems are relatively well known in the medical arts, for use in delivering or dispensing an agent, such as insulin or another prescribed medication, to a patient. Use of infusion pump therapy has been increasing, especially for delivering insulin for diabetics. Some infusion pumps can be worn on the body of a patient and implement control schemes that monitor and regulate a patient's blood glucose level in a substantially continuous and autonomous manner.

Over time, the needs of a particular patient may change. For example, an individual's insulin sensitivity and/or insulin requirements may change as he or she ages or experiences lifestyle changes. Furthermore, each individual's needs may change in a manner that is unique relative to other patients. Accordingly, routine monitoring, doctor visits and manual adjustments to device settings may be performed to accommodate changes in an individual's needs. In such situations, it may be desirable to transmit infusion pump data to another device for monitoring, analysis, processing, device diagnostics, or the like. However, it can be impractical, inconvenient, or unnecessary to transmit infusion pump data on a frequent regular basis. Rather, larger batches of data may be transmitted intermittently.

Wireless communications protocols may limit or restrict throughput and undesirably increase the duration of time required for transferring data from the infusion pump to a point where users could potentially become frustrated or discouraged from doing so as frequently as needed or desired based on their medical condition. For example, Bluetooth low energy may limit bit rates to one megabit per second or less, which is a fraction of what is achievable with modern wired communications technologies. At the same time, providing an additional or dedicated physical communications interface can undesirably impact the size, form factor, resiliency, cost, or other aspects of the infusion pump. Accordingly, it is desirable to facilitate communicating data from a fluid infusion device in an expedient manner without compromising other design aspects of the device.

BRIEF SUMMARY

Medical devices, systems, and related operating methods are provided. An embodiment of a method of operating a medical device to communicate data is provided. The method involves the medical device detecting an interfacing device coupled to the medical device, initializing a wireless communications session with the interfacing device in response to detecting the interfacing device, modulating an electrical signal between the interfacing device and the medical device to transmit data from the medical device to the interfacing device, and receiving communications from the interfacing device via the wireless communications session.

A medical device communications system is also provided. The system includes an interfacing device and a medical device. The interfacing device includes a connection arrangement for a physical communications medium and a first wireless communications module. The medical device includes a data storage element to maintain operational data, a switched resistance arrangement coupled to a terminal of the medical device, a second wireless communications module, and a control module coupled to the switched resistance arrangement and the second wireless communications module. The control module initiates a wireless communications session between the first and second wireless communications modules in response to detecting the connection arrangement being coupled to the terminal, operates the switched resistance arrangement to modulate an electrical signal on the physical communications medium in a manner corresponding to the operational data, and receives acknowledgment of the operational data from the interfacing device via the wireless communications session.

In another embodiment, a medical device is also provided. The medical device includes a supply voltage terminal, a data storage element, a switched resistance arrangement coupled to the supply voltage terminal, and a control module coupled to the switched resistance arrangement and the wireless communications module. The control module transmits operational data maintained in the data storage element by operating the switched resistance arrangement to modulate an input current at the supply voltage terminal in a manner corresponding to the operational data and receives acknowledgment of the transmitted operational data via the wireless communications module.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
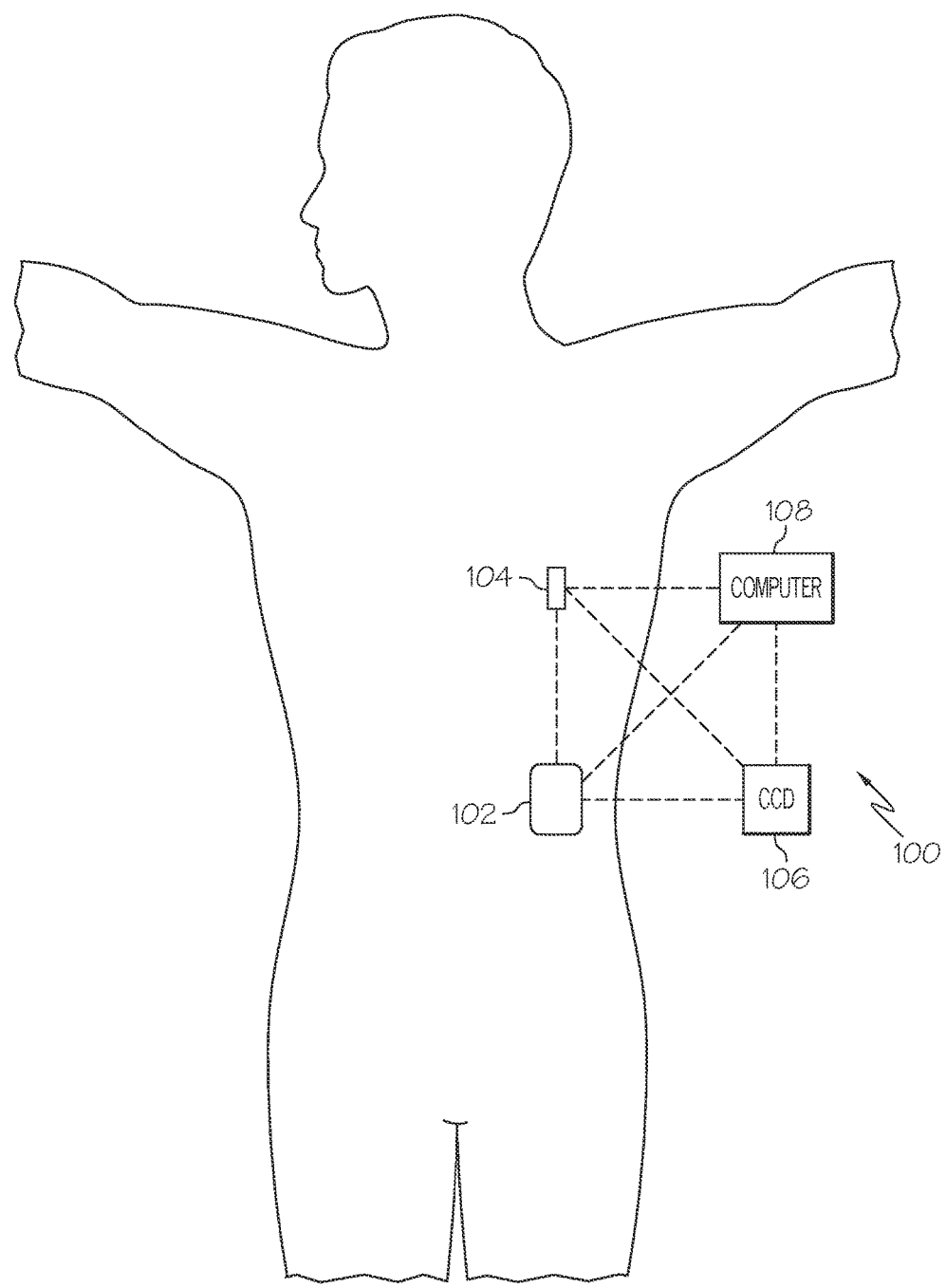
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below, primarily in the context of FIGS. 6-8, in exemplary embodiments, the fluid infusion device automatically detects coupling of an interfacing device providing a physical communications medium between the fluid infusion device and a computing device, and in response, initializes a wireless communications session with the interfacing device. Thereafter, the fluid infusion device transmits operational data stored onboard the fluid infusion device to the computing device via the interfacing device by modulating an electrical signal between the interfacing device and the infusion device in a manner corresponding to the data to be transmitted. For example, a control module of the fluid infusion device may alternately activate and deactivate a switched resistance arrangement coupled to the physical communications medium to modulate an input current to the fluid infusion device in a manner that corresponds to the bits of data being transmitted. The interfacing device receives or otherwise recognizes the transmitted bits of data based on the electrical signal through the physical communications medium and transmits or otherwise provides acknowledgments back to the infusion device via the wireless communications session. In this manner, bandwidth of the physical communications medium is not utilized for acknowledgments. Additionally, the interfacing device may request resending of any data that was not validly received.

In one exemplary embodiment, the interfacing device includes a connection arrangement that conforms to an existing receptacle within the housing of the infusion device, such as a battery receptacle, thereby obviating the need for a dedicated interface on or within the housing for the physical communications medium. In this regard, the connection arrangement may electrically connect the physical communications medium to the supply voltage terminal of the battery connector, with the switched resistance arrangement being coupled between the supply voltage terminal and a ground voltage terminal (or node) of the infusion device to modulate the input current at the supply voltage terminal. A control module of the infusion device may detect insertion of the connection arrangement in response to a voltage applied at the supply voltage terminal increasing the voltage or power supplied to the control module, and in response operate a wireless communications module of the infusion device to establish a wireless communications session with the interfacing device. The control module then locates or otherwise identifies the stored operational data to be transmitted in a data storage element (or memory), and then operates the switched resistance arrangement accordingly. In this regard, the transmitted data bits correspond to the stored data bits, but may also include error correcting codes or other bits as dictated by the encoding and/or encryption schemes being utilized for a given deployment.

In exemplary embodiments, the interfacing device includes a current sensing arrangement coupled to the physical communications medium that generates an output influenced by the input current to the infusion device, and a control module of the interfacing device is coupled to the output of the current sensing arrangement to identify or otherwise receive the bits of data being transmitted. In this regard, the interfacing device control module may perform decoding, decryption, and/or error checking corresponding to the encoding, encryption and/or error coding employed by the infusion device control module to verify or otherwise confirm that the transmitted data was validly received before either transmitting an acknowledgment or a request to resend the data via the wireless communications module.

The interfacing device control module transmits or otherwise provides the received operational data to the computing device. Thereafter, the computing device may be utilized by a user to monitor or otherwise analyze the operational data, view graphical representations of the operational data (e.g., delivery or dosage history, patient history, etc.), and the like, and based thereon, or modify infusion device settings, preferences, or other parameters.

Any modified settings data may then be uploaded to the infusion device by the computing device transmitting the data to the interfacing device control module, which, in turn, transmits the data to the infusion device via the wireless communications session with the appropriate encoding, encryption, error coding, etc. The infusion device control module stores or otherwise maintains any settings data received via the wireless communications session at the appropriate location(s) in the memory onboard the infusion device, and thereafter, utilizes that settings data during subsequent operation of the infusion device.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
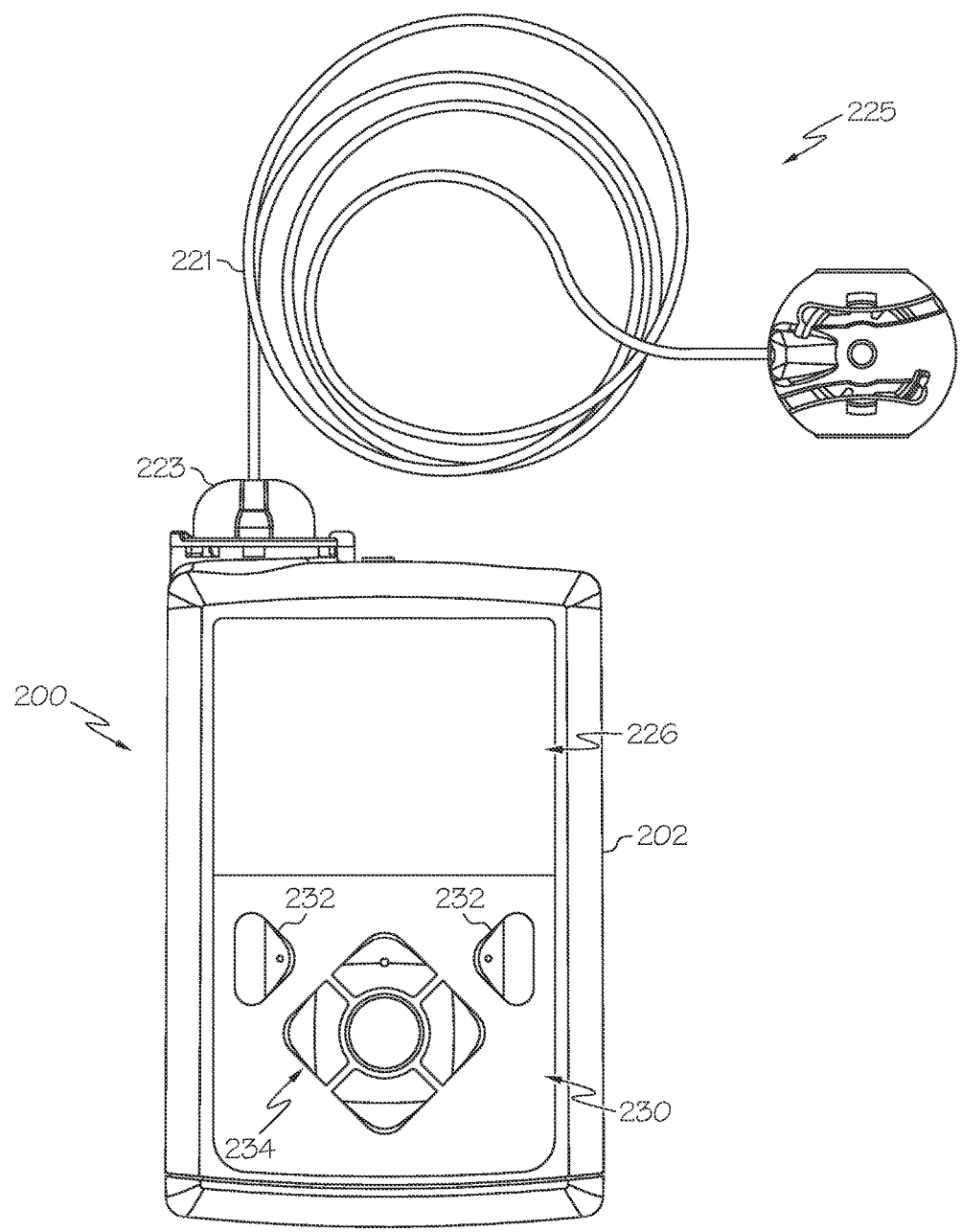
FIG. 2 depicts a plan view of an exemplary embodiment of a fluid infusion device suitable for use in the infusion system of FIG. 1.
Figure 3:
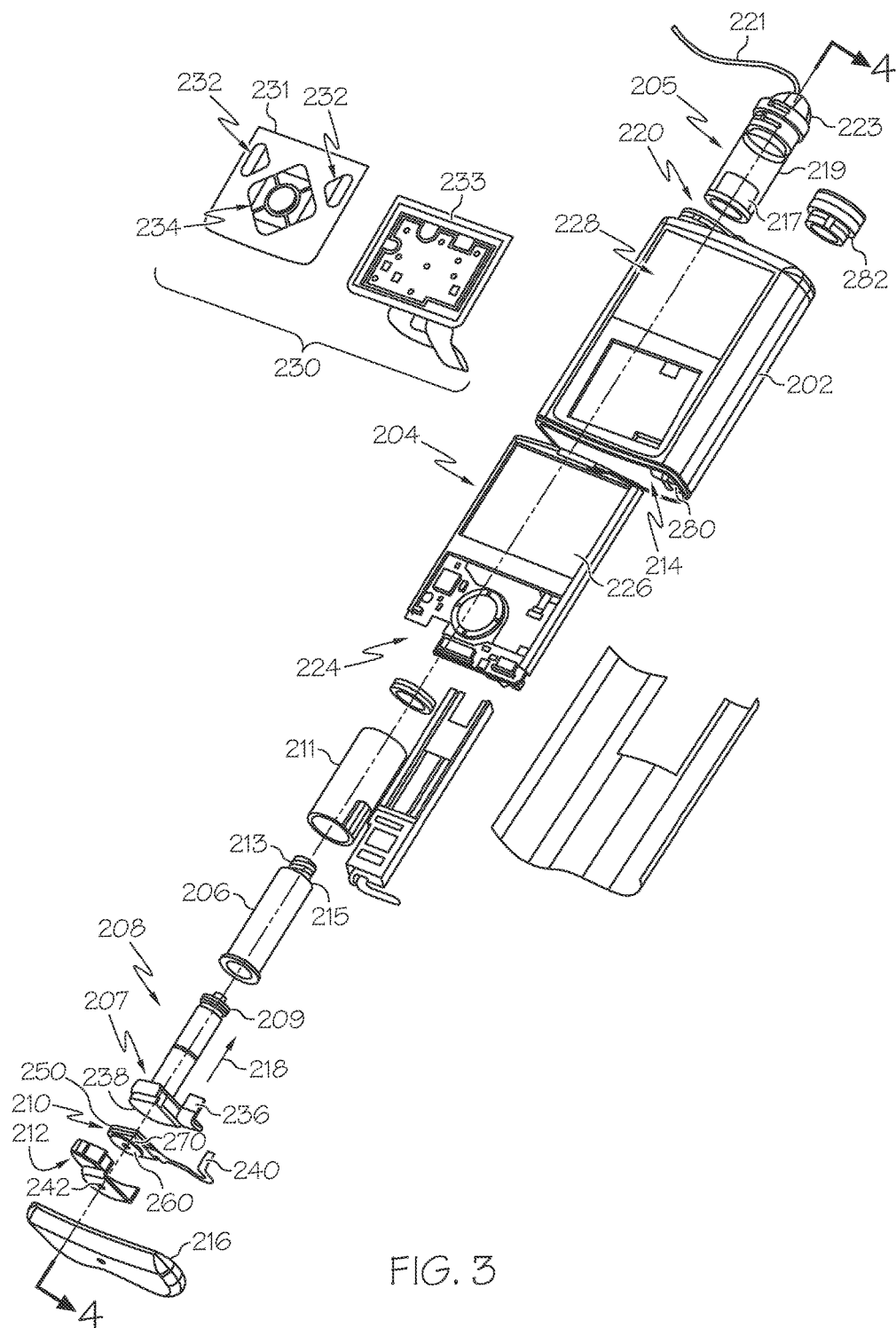
FIG. 3 is an exploded perspective view of the fluid infusion device of FIG. 2.
Figure 4:
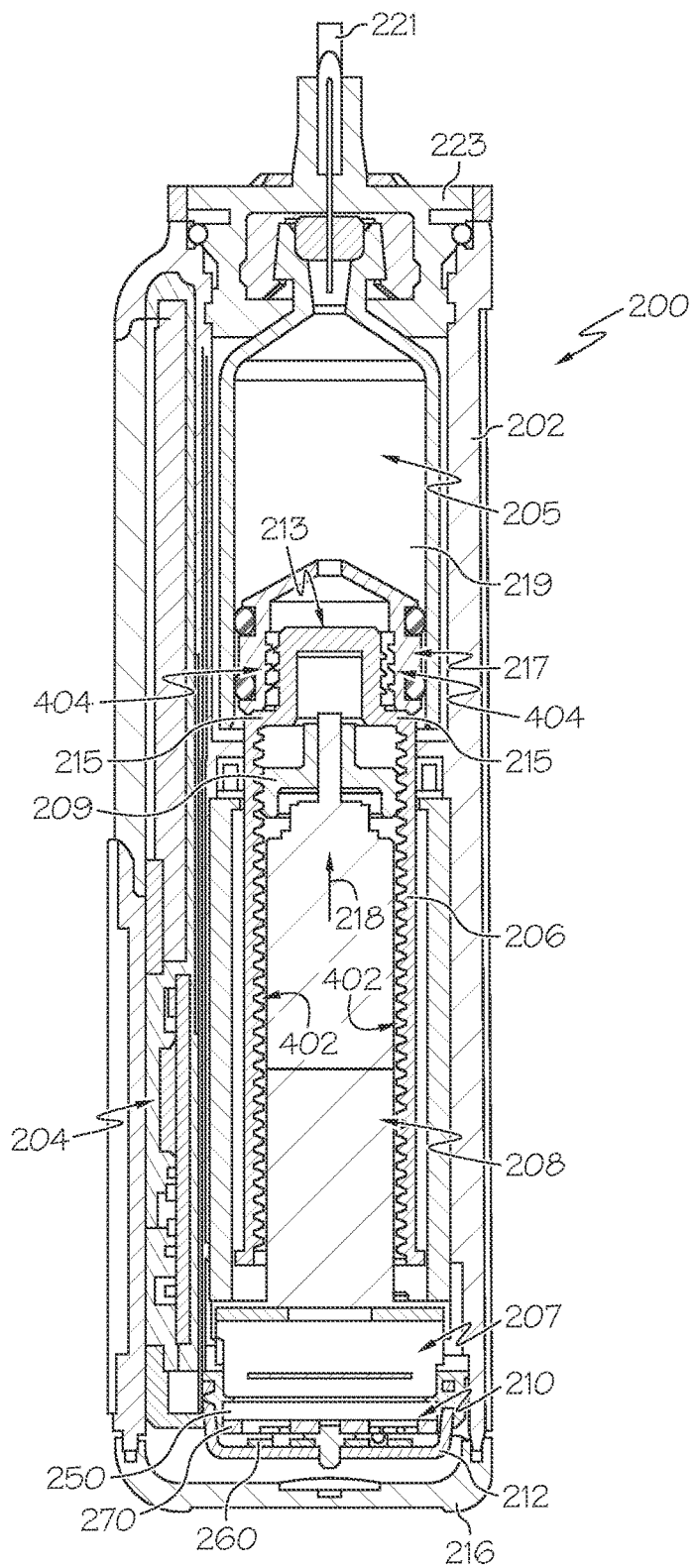
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

As illustrated in FIG. 3, the hollow interior 214 defined by the housing also includes with a portion configured to receive or otherwise conform to a battery (i.e., a battery receptacle), which mates with a connector 280 configured to establish an electrical connection from the battery to the drive system 208, the control electronics 224, the display 226 and/or other components of the infusion device 200. A battery cap 282 retains the battery within the housing 202 and engaged with the connector 280 when assembled. As described in greater detail below in the context of FIGS. 6-8, in one or more exemplary embodiments, in lieu of a dedicated physical communications interface, the battery cap 282 and any battery may be removed from the infusion device 200 and replaced with a battery emulator having substantially the same shape as the battery and an integrated cap configured to provide a physical communications interface to the control electronics 224 and/or other components of the infusion device 200. For example, the hollow interior 214 and battery connector 280 may be configured to receive and conform to a AA-sized battery, whereby the battery emulator has substantially the same size and form factor as a AA-sized battery to support insertion into the housing 202 and engagement with the battery connector 280 in a substantially similar manner as the battery. The battery cap associated with the battery emulator then retains the battery emulator engaged with the battery connector 280 while also supporting a physical interface for electrical communications to/from the control electronics 224 and/or other components of the infusion device 200 via the battery emulator and the connector 280.

Figure 5:
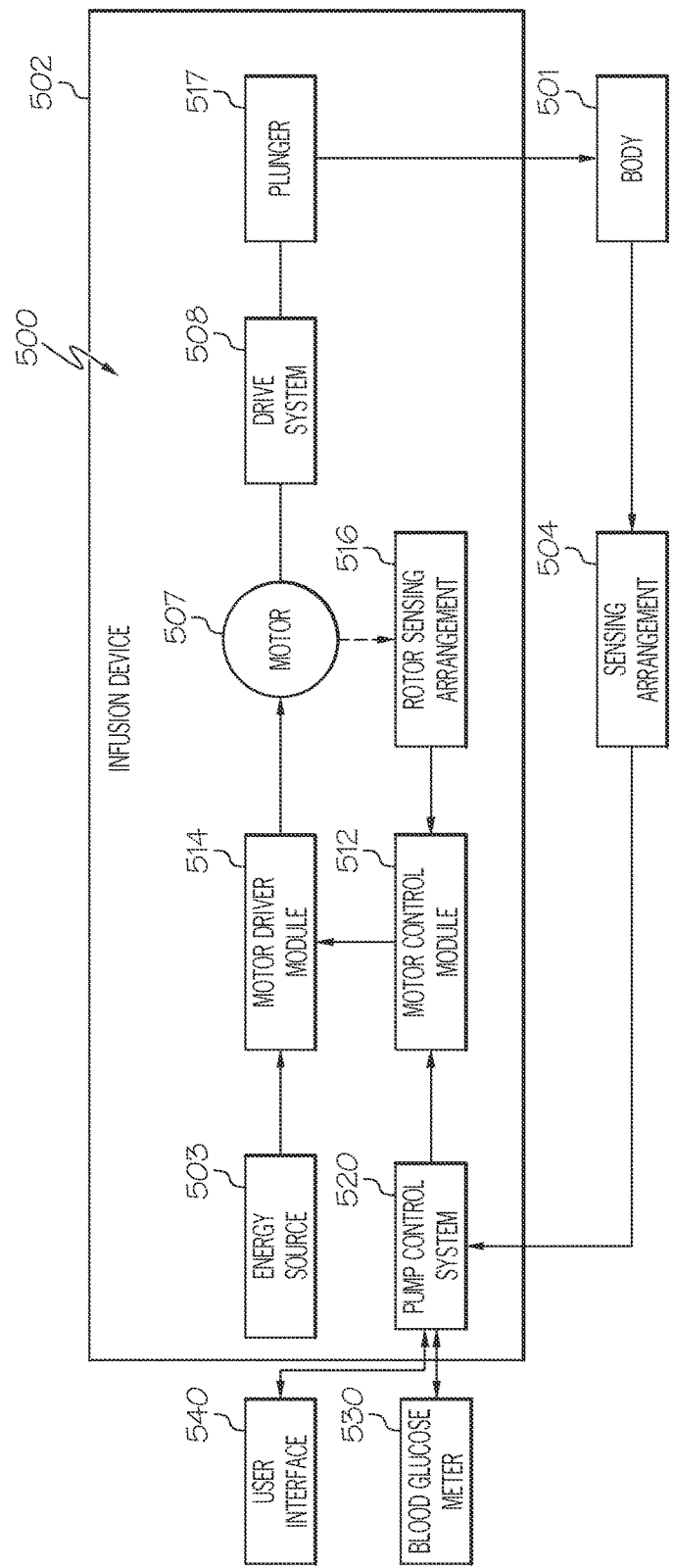
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is capable of controlling or otherwise regulating a physiological condition in the body 501 of a user to a desired (or target) value or otherwise maintain the condition within a range of acceptable values in an automated manner. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of a current glucose level in the body 501 of the user. For example, to support a closed-loop operating mode, the pump control system 520 maintains, receives, or otherwise obtains a target or commanded glucose value, and automatically generates or otherwise determines dosage commands for operating the motor 507 to displace the plunger 517 and deliver insulin to the body 501 of the user based on the difference between a sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), and/or other glucose threshold value(s) in a data storage element accessible to the pump control system 520.

The target glucose value and other threshold glucose values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108.

Figure 6:
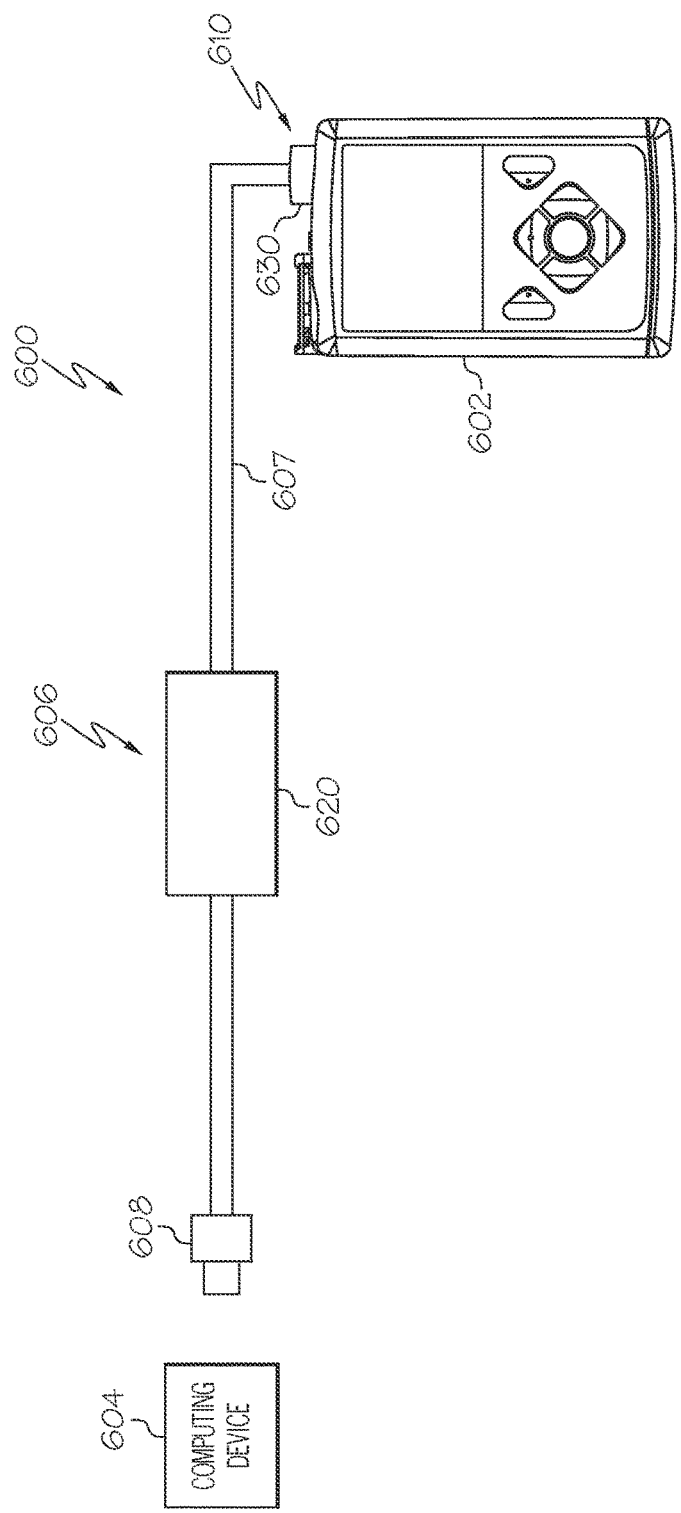
FIG. 6 is a block diagram of an exemplary medical device communications system for transferring data between a medical device and an external computing device using an interfacing device.

FIG. 6 depicts an exemplary embodiment of a system 600 for transferring data between an infusion device 602 and a computing device 604. An interfacing device 606 provides a physical communications medium 607 between the infusion device 602 and the computing device 604 while also supporting wireless communications with the infusion device 602, as described in greater detail below. In exemplary embodiments, the interfacing device 606 supports unidirectional communications from the infusion device 602 to the computing device 604 via the physical communications medium 607 while supporting bidirectional wireless communications with the infusion device 602.

The interfacing device 606 includes a first connection arrangement 608 that is coupled to the computing device 604 to provide an electrical interconnection between the computing device and the physical communications medium 607. For example, the physical communications medium 607 may be realized as a cable compatible with a universal serial bus (USB) standard, where the connection arrangement 608 is realized as a USB connector capable of mating with or otherwise inserted in a corresponding receptacle on the computing device 604. That said, it should be noted that the subject matter is not limited to a particular type of physical communications medium or connection arrangement for the computing device 604.

The interfacing device 606 also includes another connection arrangement 610 that is coupled to the infusion device 602 to provide an electrical interconnection between the infusion device 602 and the physical communications medium 607. In exemplary embodiments, the infusion device connection arrangement 610 is realized as a battery emulator integrated with a capping member 630 that can be screwed (e.g., using threads formed on or in the capping member 630) or otherwise fastened with the housing of the infusion device 602. In this regard, the battery emulator may have a form factor corresponding to the battery normally utilized in the infusion device 602 so that the battery emulator supports an electrical connection to the internal circuitry of the infusion device 602 via the terminals of the battery connector (e.g., battery connector 280) within the infusion device housing. The capping member 630 integrated with the battery emulator may similarly emulate the battery cap (e.g., battery cap 282) and hold the battery emulator engaged with the battery connector when screwed on to the infusion device 602. Additionally, the capping member 630 provides an electrical interconnection between the battery emulator and the physical communications medium 607. Thus, the infusion device connection arrangement 610 provides an electrical connection between the physical communications medium 607 and the internal electrical components of the infusion device 602 via the capping member 630 and the battery emulator engaged with the terminals of the internal battery connector.

In exemplary embodiments, the interfacing device 606 also includes circuitry 620 that manages or otherwise controls communications between the infusion device 602 and the computing device 604 via the interfacing device 606. The management circuitry 620 is arranged between the infusion device 602 and the computing device 604, and depending on the embodiment, portions of the management circuitry 620 may be integrated with the physical communications medium 607, the external device connection arrangement 608, and/or the infusion device connection arrangement 610. Thus, while FIG. 6 depicts the management circuitry 620 as being integrated with the physical communications medium 607, in various alternative embodiments, components of the management circuitry 620 may be distributed throughout the interfacing device 606 to achieve a desired form factor for the interfacing device 606.

Figure 7:
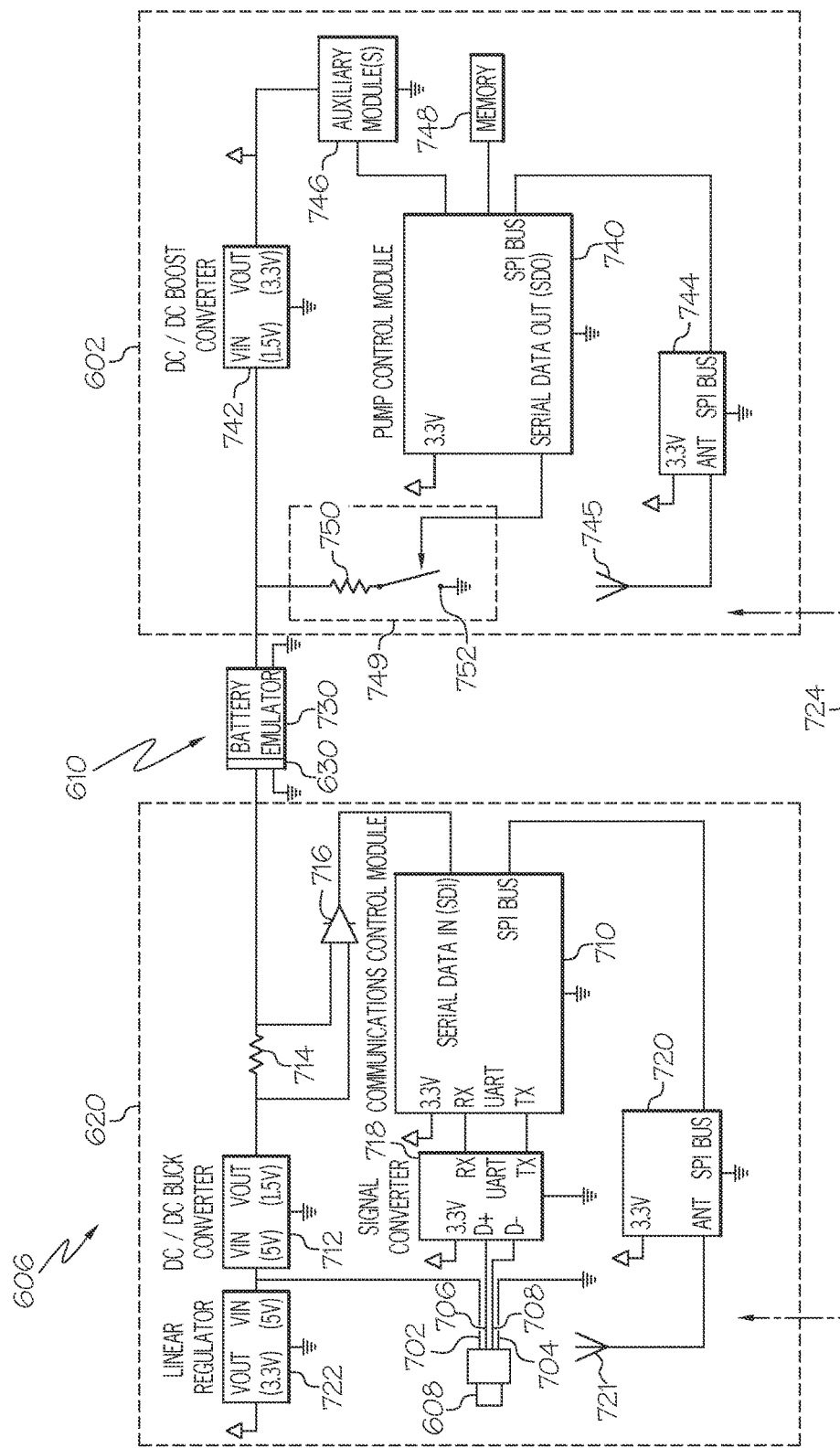
FIG. 7 is a schematic representation of the interfacing device and the medical device of FIG. 6 in one or more exemplary embodiments.

FIG. 7 depicts a schematic view of an exemplary embodiment of the management circuitry 620 interfacing with internal circuitry of the infusion device 602 via the infusion device connection arrangement 610. The illustrated embodiment depicts the external device connection arrangement 608 being realized as a USB connector including four input/output (I/O) terminals: a positive (or supply) reference voltage terminal 702, a negative (or ground) reference voltage terminal 704, and differential data signal terminals 706, 708. The management circuitry 620 includes a voltage converter 712, such as a DC-to-DC buck converter, that is coupled to the reference voltages at terminals 702, 704 and converts the voltage differential between those terminals 702, 704 to the infusion device supply voltage corresponding to battery typically utilized in the infusion device 602. For example, in the case of a 1.5 Volt AA battery being utilized in the infusion device 602 and the connection arrangement 608 being realized as a USB connector providing a 5 Volt bus voltage, the DC-to-DC buck converter 712 converts the 5 Volts from the computing device 604 to 1.5 Volts that are output or otherwise provided to the infusion device connection arrangement 610 via the portion of the physical communications medium 607 between the voltage converter 712 and the infusion device connection arrangement 610. That said, it should be noted that in various embodiments, the output voltage of the voltage converter 712 may be different from the nominal battery supply voltage for the infusion device 602, and in some cases, may be variable or adjustable (e.g., under the control of the communications control module 710) to facilitate automated detection of the interfacing device 606, communications to/from the infusion device 602, or the like. The illustrated circuitry 620 also includes a linear regulator 722 having inputs coupled to the reference voltages at terminals 702, 704 that converts the voltage differential between those terminals 702, 704 to a supply reference voltage for other components 710, 716, 718, 720 of the circuitry 620 (e.g., from 5 Volts to 3.3 Volts).

As illustrated, a resistive element 714 is electrically connected in series between the output of the voltage converter 712 (VOUT) and the infusion device connection arrangement 610 so that any current drawn from the interfacing device 606 by the infusion device 602 flows through the resistive element 714. A current sensing arrangement 716 includes inputs electrically connected to both ends of the resistive element 714 to detect or otherwise identify a voltage drop across the resistive element 714, which, in turn, is indicative of a current through the resistive element 714. The current sensing arrangement 716 compares the detected voltage to a threshold, and generates a logical high voltage output (e.g., logic '1' or 3.3 Volts) when the detected voltage is greater than the threshold, and otherwise generates a logical low voltage (e.g., logic '0' or 0 Volts) when the detected voltage is less than the threshold. In this manner, the current sensing arrangement 716 and the resistive element 714 are cooperatively configured to detect when current flows from the interfacing device 606 to the infusion device 602, where the output from the current sensing arrangement 716 corresponds to a bit of serial data transmitted by the infusion device 602, as described in greater detail below.

In exemplary embodiments, the current sensing arrangement 716 also includes, incorporates, or otherwise supports automatic gain control and offset compensation configured such that the nominal current consumption of the infusion device 602 during normal operation (and also any current consumption that is less than that amount) represents a logical low voltage output, while a current through the resistive element 714 that exceeds that nominal current consumption amount by at least a threshold amount corresponds to a logical high voltage. The threshold amount can be chosen such that variations across different instances of the infusion device 602 attributable to component tolerances or other manufacturing variances are unlikely to result in the current sensing arrangement 716 generating a logical high voltage output when the switching element 752 is not activated.

The circuitry 620 also includes a communications control module 710 having a serial data input (SERIAL DATA IN) that is coupled to the output of the current sensing arrangement 716 to receive or otherwise identify bits of serial data transmitted by the infusion device 602. The communications control module 710 also includes another serial data input/output interface configured to communicate with a wireless communications module 720 (or wireless transceiver) of the interfacing device 606. For example, the communications control module 710 and the wireless transceiver 720 may each include a serial peripheral interface (SPI) for communicating via a SPI bus coupled between the modules 710, 720. The wireless transceiver 720 is also connected to an antenna 721 to facilitate wireless communications with the infusion device 602, as described in greater detail below. In one embodiment, the wireless communications module 720 is configured to support communications via a Bluetooth low energy (BLE) communications protocol, standard, or specification. The illustrated communications control module 710 also includes transmit and receive I/O interfaces which are coupled to corresponding receive and transmit I/O interfaces of a signal conversion module 718, which, in turn, converts single-ended signals from the communications control module 710 to differential data signals provided to the computing device 604 via the USB connector 608, and vice versa. For example, the communications control module 710 may include universal asynchronous receiver/transmitter (UART) interfaces coupled to corresponding UART interfaces on the signal converter 718 which converts between UART data signals and USB data signals. That said, in some embodiments, the signal converter 718 may be integrated into the communications control module 710.

Depending on the embodiment, the communications control module 710 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the communications control module 710, or in any practical combination thereof. For example, the communications control module 710 may include or otherwise access a data storage element or memory, which may be realized using any sort of non-transitory computer-readable medium capable of storing programming instructions for execution by the communications control module 710. The computer-executable programming instructions, when read and executed by the communications control module 710, cause the communications control module 710 to implement, support, or otherwise perform the tasks, operations, functions, and processes described in greater detail below.

Still referring to FIGS. 6-7, the infusion device connection arrangement 610 electrically connects the voltage output from the voltage converter 712 downstream of the current-sensing resistive element 714 to a supply voltage input node of the infusion device 602 via the battery connector (e.g., battery connector 280) within the infusion device 602. In this regard, the capping member 630 is connected to the physical communications medium 607 to receive the negative reference (or ground) voltage for the circuitry 620 from terminal 704 and the supply voltage for the infusion device 602 from the end of the current-sensing resistive element 714 opposite the voltage converter 712. The battery emulator 730 is electrically connected to the capping member 630 to receive the ground and supply voltages, and in turn, provides those to the appropriate terminals (or nodes) of the battery connector within the infusion device 602. In this manner, the infusion device connection arrangement 610 merely provides an interface between the internal circuitry of the infusion device 602 and the physical communications medium 607. The supply voltage input to the infusion device 602 is provided to a voltage conversion module 742, such as a DC-to-DC boost converter, that converts the input supply voltage (e.g., 1.5 Volts) to a different supply reference voltage (e.g., 3.3 Volts) that powers various elements 740, 744, 746 of the infusion device 602.

As illustrated in FIG. 7, the internal infusion device circuitry includes a switched resistance arrangement having a resistive element 750 electrically connected between the input supply voltage node and the ground voltage node via a switching element 752 configured electrically in series with the resistive element 750. In this regard, the switched resistance arrangement 749 is effectively connected between the battery terminals (e.g., connector 280) of the infusion device 602. The switching element 752 is operated to regulate current flow through the resistive element 750, which, in turn, influences the current that flows through the current-sensing resistive element 714 via the connection arrangement 610. A control module 740 of the infusion device 602 (alternatively referred to herein as the pump control module) includes a serial data output interface (SERIAL DATA OUT) that is coupled to the switching element 752 to control activation of the switching element 752, and thereby transmit serial data bits to the communications control module 710, as described in greater detail below. The pump control module 740 also includes another serial data input/output interface configured to communicate with a wireless communications module 744 of the infusion device 602. For example, the pump control module 740 and the wireless transceiver 744 may each include a serial peripheral interface (SPI) for communicating via a SPI bus coupled between the modules 740, 744. The wireless transceiver 744 is also connected to an antenna 745 to facilitate wireless communications with the wireless transceiver 720 of the interfacing device 606, as described in greater detail below.

The pump control module 740 may also include one or more additional I/O interfaces coupled to various additional or auxiliary modules 746 (e.g., a motor driver module 507, a user interface 530, a display 226, and/or the like) of the infusion device 602 to control operation of those modules 746. As described in greater detail below, when transmitting data to the computing device 604 via the interfacing device 606, the pump control module 740 signals, commands, instructs, or otherwise operates the auxiliary modules 746 in respective operating modes that result in substantially constant current consumption by the auxiliary modules 746 during transmission, so that the only fluctuations in the current flowing through the resistive element 714 is attributable to operation of the switching element 752. In this regard, during transmission, the pump control module 740 may also operate some of its own internal components so that the current consumed by the pump control module 740 is also substantially constant during operation of the switching element 752.

Again, depending on the embodiment, the pump control module 740 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 740, or in any practical combination thereof For example, the pump control module 740 may include or otherwise access a data storage element or memory, which may be realized using any sort of non-transitory computer-readable medium capable of storing programming instructions for execution by the pump control module 740. The computer-executable programming instructions, when read and executed by the pump control module 740, cause the pump control module 740 to implement, support, or otherwise perform the tasks, operations, functions, and processes described in greater detail below.

In exemplary embodiments, the pump control module 740 is coupled to a data storage element (or memory) 748 that stores or otherwise maintains operational data pertaining to operations of the infusion device 602 along with settings data that controls or otherwise dictates operations of the infusion device 602. The operational data may include, for example, historical delivery or dosage information, historical blood glucose and/or sensor glucose measurements, alarm history, trace data, event logs, and/or other information that may be utilized to analyze, diagnose and/or debug operation of the infusion device 602. The settings data may include, for example, user-configurable alarm thresholds or settings, user-configurable delivery settings (e.g., total daily dose, a basal infusion rate, or the like), control parameters (e.g., closed-loop proportional-integral-derivative (PID) gain parameters), and the like. As described in greater detail below, in exemplary embodiments, some or all of the operational data may be downloaded to the computing device 604 from the infusion device 602 via the physical communications medium 607 for analysis on the computing device 604, and conversely, modified or updated settings data may be uploaded to the infusion device 602 from the computing device 604 via a wireless communications session.

It should be understood that FIG. 7 is a simplified representation of the interfacing device 606 and internal circuitry of the infusion device 602 for purposes of explanation and ease of description, and FIG. 7 is not intended to limit the application or scope of the subject matter in any way. Thus, although FIG. 7 depicts direct electrical connections between components, alternative embodiments may employ intervening circuit elements and/or components while functioning in a substantially similar manner.

Figure 8:
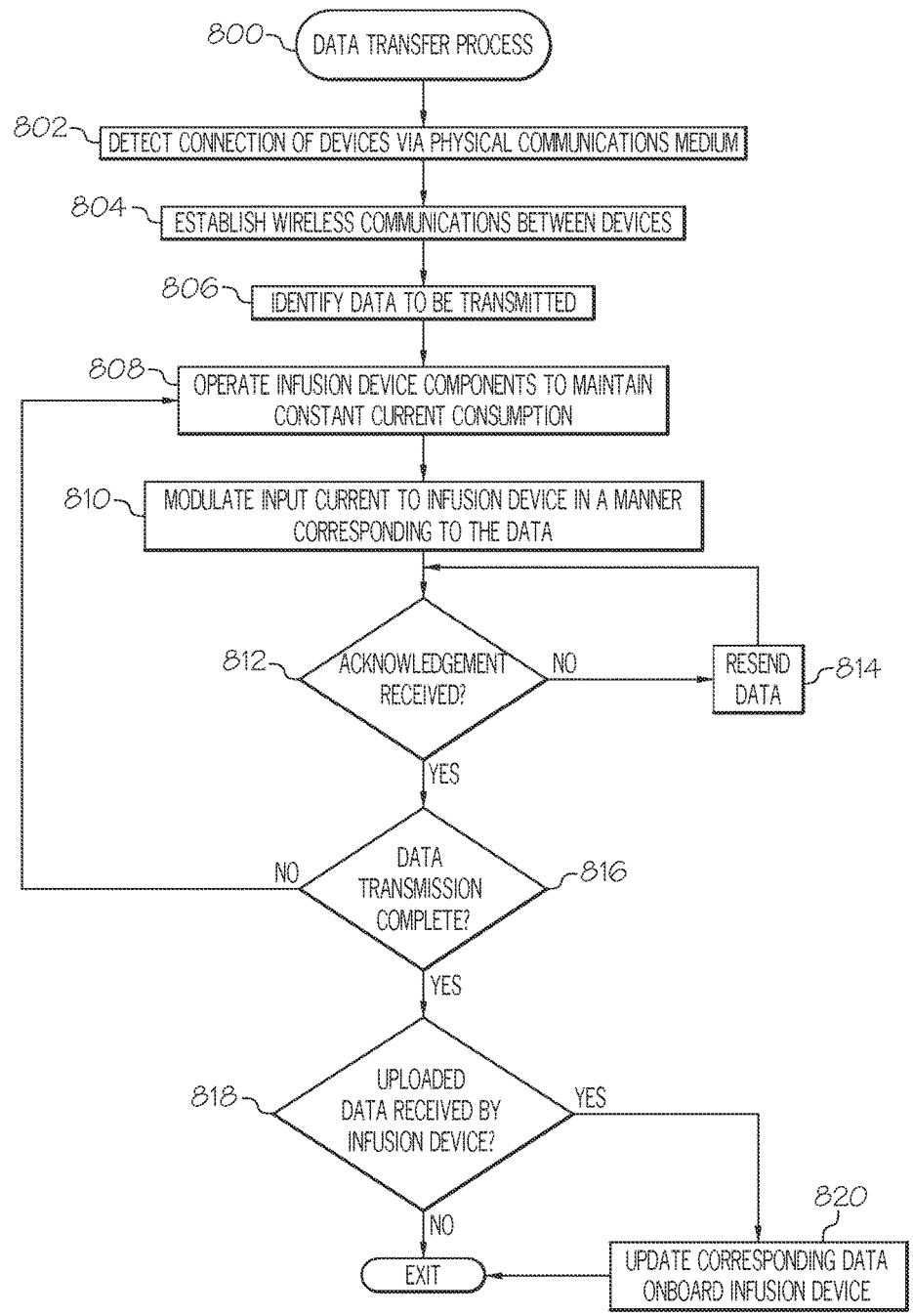
FIG. 8 is a flow diagram of an exemplary data transfer process suitable for use with the medical device communications system of FIG. 6 in one or more exemplary embodiments.

FIG. 8 depicts an exemplary data transfer process 800 suitable for transferring data between two devices, such as between infusion device 602 and computing device 604. The various tasks performed in connection with the data transfer process 800 may be performed by hardware, firmware, software executed by processing circuitry, or any combination thereof. For illustrative purposes, the following description refers to elements mentioned above in connection with FIGS. 1-7. In practice, portions of the data transfer process 800 may be performed by different elements of data communications system 600, such as, for example, the infusion device 602, the computing device 604, the interfacing device 606, the communications control module 710, the current sensing arrangement 716, the signal converter 718, the wireless communications module 720, the pump control module 740, the wireless communications module 744, and/or the switching element 752. It should be appreciated that the data transfer process 800 may include any number of additional or alternative tasks, the tasks need not be performed in the illustrated order and/or the tasks may be performed concurrently, and/or the data transfer process 800 may be incorporated into a more comprehensive procedure or process having additional functionality not described in detail herein. Moreover, one or more of the tasks shown and described in the context of FIG. 8 could be omitted from a practical embodiment of the data transfer process 800 as long as the intended overall functionality remains intact.

Referring to FIG. 8 and with continued reference to FIGS. 6-7, the illustrated process 800 begins by detecting or otherwise identifying establishment of an electrical connection between devices via a physical communications medium, and in response, establishing or otherwise initializing wireless communications between the devices (tasks 802, 804). For example, the pump control module 740 may detect a connection with a computing device 604 via a physical communications medium 607 in response to receiving a supply voltage from the voltage converter 742 indicative of both device connection arrangements 608, 610 being inserted in the respective devices 602, 604 concurrently. In some embodiments, the voltage converter 712 may be configured to provide a voltage that deviates from the nominal battery supply voltage by an amount that indicates, to the pump control module 740, that something other than a battery is inserted into the infusion device 602. For example, when the nominal battery supply voltage is 1.5 Volts, the voltage converter 712 may be configured to provide, at least initially, a 2.5 Volt output to the physical communications medium 607. The pump control module 740 may monitor or otherwise identify the difference from the nominal battery supply voltage at the connector 280, and thereby detect or otherwise identify the establishment of an electrical connection with an external device. In such embodiments, the communications control module 710 may be coupled to the voltage converter 712 and configured to command, signal, or otherwise operate the voltage converter 712 to adjust the output voltage on the physical communications medium 607 down to the nominal battery supply voltage after establishment of a wireless communications session with the infusion device 602.

In response to detecting an electrical connection to the interfacing device 606 via the physical communications medium 607, the pump control module 740 may automatically signal, command, or otherwise operate the wireless communications module 744 to attempt to establish wireless communications with the interfacing device 606. For example, the pump control module 740 may cause the wireless communications module 744 to perform a discovery process to identify other devices that are proximate to or otherwise in the vicinity of the infusion device 602. Similarly, when the connection arrangement 608 establishes an electrical connection with the computing device 604, the communications control module 710 may automatically signal, command, or otherwise operate the wireless communications module 720 to discover or otherwise identify the infusion device 602. Upon the wireless communications modules 720, 744 discovering one another, a pairing process may be performed by the wireless communications modules 720, 744 to obtain and maintain unique identification information associated with the other wireless communications module 720, 744 for establishing a peer-to-peer wireless communications session 724 between the infusion device 602 and the interfacing device 606. Thus, upon the device connection arrangements 608, 610 being inserted in the respective devices 602, 604 concurrently, the interfacing device 606 and the infusion device 602 may automatically establish wireless communications.

In one or more embodiments, the pump control module 740 implements one or more security measures to prevent establishment of a wireless communications session with untrusted devices. For example, in response to discovering a wireless communications module 720 associated with another device, the pump control module 740 may automatically operate the switching element 752 to transmit or otherwise provide, via the physical communications medium 607, data bits corresponding to authentication information used for pairing with the wireless communications module 744. For example, the authentication information may be a secret code or key, such as a number, identifier, or the like that is uniquely associated with the infusion device 602 or a random number dynamically generated by the pump control module 740 upon each iteration of the process 800. In practice, some embodiments could employ even more robust authentication schemes as desired. In the absence of the pump control module 740 receiving the authentication information from the discovered wireless communications module via the pump wireless communications module 744 within a timeout period, the pump control module 740 may automatically command, signal, instruct, or otherwise operate the wireless communications module 744 to deny any pairing attempts with the discovered wireless communications module. Thus, the pump control module 740 may only allow establishment of wireless communications sessions with an interfacing device 606 that includes a physical communications medium 607 coupled to the infusion device 602.

The illustrated process 800 continues by identifying or otherwise determining the data to be uploaded or otherwise transmitted from the infusion device (task 806). In some embodiments, the pump control module 740 may automatically identify or determine the data to be transmitted to the computing device 604. For example, based on settings for the infusion device 602 (which could be user-configurable) stored in memory 748 of the infusion device 602, the infusion device 602 may automatically transmit particular types of data (or certain data sets) from the memory 748 whenever the infusion device 602 is connected to a computing device 604 via the interfacing device 606. In other embodiments, a user may manipulate one or more user interfaces associated with the infusion device 602 to select or otherwise identify which types of data or data sets that the user would like to upload to the computing device 604. In yet other embodiments, a user may manipulate one or more user interfaces associated with the computing device 604 to select or otherwise identify which types of data or data sets that the user would like to download to the computing device 604 from the infusion device 602. In such embodiments, upon selection of the data to be transmitted, the computing device 604 may transmit or otherwise provide an indication of the selected data to the communications control module 710 (via the signal converter 718), which, in turn, commands or otherwise operates the wireless communications module 720 to transmit the indication of the selected data to the pump control module 740 via the wireless communications session 724.

After the data to be transmitted is identified, the data transfer process 800 continues by operating components of the infusion device to consume a substantially constant current while concurrently modulating the input current to the infusion device in a manner corresponding to the data identified for transmission (tasks 808, 810). For example, the control module 740 may command, instruct, or otherwise operate other modules 746 of the infusion device 602 so that their current consumption or demands do not fluctuate while concurrently activating and deactivating the switching element 752 to modulate the current flow to the infusion device 602 in a manner that corresponds to the bits of the data being transmitted. For example, to transmit a logical high bit (or logic '1'), the pump control module 740 may close, turn on, or otherwise activate the switching element 752 to draw current through the resistive element 750, which, in turn, increases current through the resistive element 714 and causes the current sensing arrangement 716 to generate a logical high bit (or logic '1') at a serial data input to the communications control module 710. Conversely, to transmit a logical low bit (or logic '0'), the pump control module 740 may open, turn off, or otherwise deactivate the switching element 752 to prevent current through the resistive element 750, which, in turn, decreases current through the resistive element 714 and causes the current sensing arrangement 716 to generate a logical low bit (or logic '0') at the serial data input to the communications control module 710. In addition to transmitting bits of data, the pump control module 740 may also transmit bits according to various encryption and/or encoding schemes that may be implemented to improve security, reliability, and the like. For example, the pump control module 740 may employ error correcting codes while also encrypting or encapsulating data from the memory 748 before transmission via the physical communications medium 607.

In exemplary embodiments, the data transfer process 800 verifies or otherwise confirms the transmitted data was received via the physical communications medium and retransmitting any data that was not validly received from the infusion device (tasks 812, 814). In one or more exemplary embodiments, the communications control module 710 receives the serialized data transmission from the pump control module 740 via the current sensing arrangement 716 and performs the error detection, decrypting and/or decoding corresponding to the encoding and/or encryption performed by the pump control module 740 to obtain the raw data intended to be transmitted from the infusion device 602. In this regard, when the communications control module 710 identifies or otherwise determines the data was successfully received and decoded and/or decrypted, the communications control module 710 may automatically transmit or otherwise provide an acknowledgment message to the control module 740 using the wireless communications session 724 established via the wireless communications module 720. Conversely, when the communications control module 710 detects or otherwise identifies an error or other failure to accurately receive, decode, or decrypt the raw data, the communications control module 710 may fail to provide an acknowledgment message. In the absence of receiving an acknowledgment message via the wireless communications module 744 within a prescribed timeout period, the pump control module 740 may automatically operate the switching element 752 to resend the unacknowledged data to the interfacing device 606. It should be noted that while the subject matter is described here in the context of the communications control module 710 performing error detection, decryption and/or decoding and initiating the transmission of acknowledgment messages back to the infusion device 602, in alternative embodiments, the computing device 604 may perform error detection, decryption and/or decoding and instruct the communications control module 710 when to send acknowledgment messages.

In exemplary embodiments, the data transfer process 800 continues operating components of the infusion device to consume substantially constant current while concurrently modulating the input current to the infusion device and monitoring for corresponding acknowledgment messages until identifying or otherwise determining that the entirety of the selected data has been transmitted and received by the computing device (tasks 808, 810, 812, 814, 816). The illustrated process 800 also identifies or otherwise determines whether the infusion device has received data uploaded from the computing device, and in response, updates or otherwise modifies the stored data onboard the infusion device corresponding to the received data (tasks 818, 820). In an exemplary embodiment, after a user of the computing device 604 downloads and reviews operational data from the infusion device 602 (e.g., historical delivery and/or dosage data, alarm history, historical blood glucose measurement data, trace data, and/or the like), the user may manipulate a user interface associated with the computing device 604 to modify aspects of pump operation. For example, the computing device 604 may present a graphical user interface (GUI) that includes graphical representations of the data downloaded from the infusion device 602 along with GUI elements that allow a user to modify alarm thresholds or settings, delivery settings or control parameters (e.g., total daily dose amounts, closed-loop gain parameters, basal infusion rates, and the like), or other aspects of the infusion device operation and then upload data corresponding to the modification to the infusion device 602 via the interfacing device 606. In this regard, the signal converter 718 converts the differential data signals received from the computing device into single-ended data signals provided to the communications control module 710, which, in turn, provides a corresponding serialized data stream (with whatever encoding, encryption and/or error correcting codes being utilized) to the wireless communications module 720 for transmission to the infusion device 602 via the wireless communications session 724. Thereafter, in response to receiving indication of modified settings data, the control module 740 may overwrite the corresponding data in the memory 748 by storing or otherwise maintaining the received data from the computing device 604 in lieu of the preceding settings data.

It should be appreciated that the wireless communications session 724 between the devices 602, 606 may be persistently maintained while the devices 602, 604 are concurrently connected via the interfacing device 606 and/or physical communications medium 607 to transmit any desired amount of data between the devices 602, 604. However, upon one of the connection arrangements 608, 610 being decoupled from its respective device 602, 604, power to at least one of the wireless communications modules 720, 744 will be removed, thereby terminating the wireless communications session 724. That said, the physical communications medium 607 allows for relatively larger amounts of data to be securely transmitted from the infusion device 602 to the computing device 604 with a consistent and reliable throughput, and potentially in a shorter duration of time than could be achieved via the wireless communications session 724. Additionally, receipt acknowledgments from the communications control module 710 may be provided to the control module 740 independent of the physical communications medium 607 (e.g., via a wireless communications medium), thereby allowing the data to be communicated with improved reliability without compromising the bandwidth of the physical communications medium 607. Thus, the interfacing device 606 provides a convenient means for users to periodically (e.g., weekly, biweekly, monthly, or the like) download a bulk of pump operational data to a computing device 604 for more comprehensive review and/or analysis in a manner that is relatively quick, secure, and reliable.

For the sake of brevity, conventional techniques related to wireless communications, serial bus communications, pairing, data encoding, data transmission, modulation, current sensing, glucose sensing and/or monitoring, closed-loop glucose control, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A system comprising:
an interfacing device comprising:
   a connection arrangement for a physical communications medium; and
   a first wireless communications module; and
a medical device comprising:
   a data storage element to maintain operational data;
   a switched resistance arrangement coupled to a terminal of the medical device;
   a second wireless communications module; and
   a control module coupled to the switched resistance arrangement and the second wireless communications module to initiate a wireless communications session between the first and second wireless communications modules in response to detecting the connection arrangement coupled to the terminal, operate the switched resistance arrangement to modulate an electrical signal on the physical communications medium in a manner corresponding to the operational data, and receive acknowledgment of the operational data from the interfacing device via the wireless communications session.

2. The system of claim 1, wherein the interfacing device further comprises a sensing arrangement electrically in series with the physical communications medium and the connection arrangement to produce an output influenced by the electrical signal.

3. The system of claim 2, wherein the interfacing device further comprises a second control module coupled to the first wireless communications module and the output of the sensing arrangement to receive the operational data based on the output of the sensing arrangement and transmit the acknowledgment in response to receiving the operational data.

4. The system of claim 2, wherein:
the connection arrangement conforms to a battery receptacle within a housing of the medical device; and
the terminal comprises a battery connector.

5. The system of claim 1, wherein the interfacing device further comprises:
a second connection arrangement for the physical communications medium; and
a converter module coupled between the second connection arrangement and the connection arrangement to convert an input voltage to the second connection arrangement to a battery supply voltage for the medical device.

6. The system of claim 5, wherein the interfacing device further comprises:
a sensing arrangement electrically in series with the physical communications medium between the converter module and the connection arrangement, the sensing arrangement producing an output influenced by the electrical signal; and
a second control module coupled to the first wireless communications module and the output of the sensing arrangement to receive the operational data based on the output of the sensing arrangement and transmit the acknowledgment in response to receiving the operational data.

7. A medical device comprising:
a supply voltage terminal;
a data storage element;
a switched resistance arrangement coupled to the supply voltage terminal;
a wireless communications module; and
a control module coupled to the switched resistance arrangement and the wireless communications module to transmit operational data maintained in the data storage element by operating the switched resistance arrangement to modulate an input current at the supply voltage terminal in a manner corresponding to the operational data and receive acknowledgment of the transmitted operational data via the wireless communications module.

8. The medical device of claim 7, wherein the control module initiates a wireless communications session via the wireless communications module prior to transmitting the operational data.

9. The medical device of claim 8, wherein the control module receives indication of the operational data to be transmitted via the wireless communications session prior to transmitting the operational data.

10. The medical device of claim 7, further comprising a motor operable to deliver fluid to a body of a user, the fluid influencing a physiological condition of the user, wherein the operational data comprises historical delivery data corresponding to operation of the motor.

* * * * *